(12) United States Patent
Waycuilis

(10) Patent No.: US 7,064,238 B2
(45) Date of Patent: Jun. 20, 2006

(54) CONVERSION OF ALKANES TO OXYGENATES

(75) Inventor: John J. Waycuilis, Cypress, TX (US)

(73) Assignee: Marathon Oil Company, Houston, TX (US)

(*) Notice: Subject to any disclaimer, the term of this patent is extended or adjusted under 35 U.S.C. 154(b) by 362 days.

(21) Appl. No.: 10/750,984

(22) Filed: Jan. 2, 2004

(65) Prior Publication Data

US 2006/0009662 A1   Jan. 12, 2006

(51) Int. Cl.
*C07C 41/01* (2006.01)
*C07C 29/00* (2006.01)

(52) U.S. Cl. .............. 568/671; 568/694; 568/695; 568/895; 568/896; 568/840; 423/463; 423/491; 423/593; 423/594; 423/595; 423/598; 423/599

(58) Field of Classification Search ............... 568/671, 568/694, 695, 895, 896, 840; 423/463, 491, 423/593, 594, 595, 598, 599
See application file for complete search history.

(56) References Cited

U.S. PATENT DOCUMENTS

| | | | |
|---|---|---|---|
| 3,210,152 A * | 10/1965 | Helden et al. ............ | 423/22 |
| 5,243,098 A | 9/1993 | Miller et al. ............ | 568/893 |
| 5,334,777 A | 8/1994 | Miller et al. ............ | 568/859 |
| 5,998,679 A | 12/1999 | Miller ................ | 568/859 |
| 6,462,243 B1 | 10/2002 | Zhou et al. ............ | 568/893 |
| 6,472,572 B1 | 10/2002 | Zhou et al. ............ | 568/893 |
| 6,525,230 B1 | 10/2002 | Grosso ............... | 568/891 |
| 2003/0069452 A1* | 4/2003 | Sherman et al. ........ | 568/694 |

* cited by examiner

*Primary Examiner*—Rosalynd Keys
(74) *Attorney, Agent, or Firm*—Jack E. Ebel; Rodney F. Brown

(57) ABSTRACT

A process is provided for converting an alkane to an oxygenated product by passing an alkane gas over a first fixed bed containing a higher valence bromide salt to produce an alkyl bromide, a hydrobromic acid, and a lower valence bromide salt. The alkyl bromide and hydrobromic acid are conveyed as a gas to a second fixed bed containing a metal oxide and are passed over the second fixed bed to produce the first bromide salt and the oxygenated product. The metal oxide in the second fixed bed is regenerated by passing oxygen over the second fixed bed producing the metal oxide and bromine. The bromine is conveyed as a gas from the second fixed bed to the first fixed bed. The first bromide salt of the first fixed bed is regenerated by passing the bromine over the first fixed bed producing the first bromide salt.

33 Claims, 2 Drawing Sheets

CONVERSION OF ALKANES TO OXYGENATES

TECHNICAL FIELD

The present invention relates generally to the conversion of natural gas to liquid hydrocarbon products, and more particularly to the conversion of alkanes to liquid oxygenates.

BACKGROUND OF THE INVENTION

Natural gas is a relatively low density material composed primarily of alkane compounds, which are alternately termed paraffins. Large deposits of natural gas are found in numerous regions of the world, many of which are relatively unpopulated and lack significant markets for natural gas. It is possible to transport the natural gas to more highly populated regions where there is greater market demand for the natural gas. However, there are a number of practical and economic considerations which limit the feasibility of transporting natural gas long distances. Foremost is the fact that many remote regions, which possess large natural gas deposits, lack gas pipeline infrastructures for transporting natural gas to more highly populated regions. Even where gas pipeline infrastructures are present, pipeline transport of natural gas is often prohibitively expensive for long distances due to the low density of natural gas.

Natural gas can alternatively be transported as compressed gas in large vessels aboard transport vehicles, such as trucks, rail cars, or ships. However, transport of compressed natural gas in accordance with this alternative is likewise often prohibitively expensive for long distances. Natural gas can be more economically transported over long distances if the natural gas is first cryogenically processed to liquified natural gas (LNG). However, this alternative is not entirely satisfactory because the high-pressure cryogenic liquifaction process is expensive and LNG transport is often impractical because there are only a limited number of facilities which are equipped to ship or receive high-pressure and low-temperature LNG. As such, a need continues to exist for a practical and economically feasible means of transporting natural gas over long distances from remote regions to regions where there is substantial market demand.

One approach which has long been considered as a potential solution to the high cost of transporting natural gas over long distances is to first chemically convert the natural gas to heavier liquid hydrocarbon products having the same or greater utility than the natural gas from which the products are derived. The resulting liquid hydrocarbon products can be economically transported using the same established infrastructure, which is used to transport conventional liquid hydrocarbons such as crude oil, gasoline, jet fuel and the like.

A class of liquid hydrocarbons termed oxygenates, which includes alcohols and ethers, such as methanol, ethanol, dimethyl ether, and the like, has broad utility as chemical feedstocks, solvents, propellants, and fuels. Oxygenates are particularly desirable as fuels for reciprocating engines and gas turbines in transportation and stationary power generation applications because oxygenates have clean burning characteristics (i.e., oxygenates generate low-emission exhaust when burned). Furthermore, oxygenates can be transported at relatively low cost.

Chemical conversion processes are well known for converting natural gas to oxygenates. For example, various natural gas reforming processes are used in combination with catalytic synthesis processes, such as the Lurgi low-pressure methanol process, to produce oxygenates, such as methanol, from natural gas. Presently utilized reforming processes are relatively inefficient, producing large amounts of waste heat and unwanted byproducts such as $CO_2$. In addition, the initial capital investment required for such processes is extremely high. Present reforming and methanol synthesis processes operate at high temperatures and pressures also result in high production costs. Accordingly, the substantial cost of methanol obtained from such conventional production technology generally restricts methanol to higher value uses than fuels. The primary applications for synthesized methanol are chemical feedstocks and solvents, although synthesized methanol does have some limited applications as an additive to conventional crude oil-derived fuels and as a neat fuel in a few demonstration or niche-market applications.

It is apparent that the above-recited need for a practical and economically feasible means of transporting natural gas over long distances can be solved by a low-cost process for converting alkanes, such as methane, ethane, and the like, found in natural gas to the corresponding alcohols and ethers, such as methanol, ethanol, and the like. Not only are alcohols and ethers valuable products, but as liquids they have a relatively high density which renders them more economically transportable than natural gas over long distances. Accordingly, the present invention recognizes a need for a low-cost process for converting alkanes to oxygenates.

It is generally an object of the present invention to provide a process for converting alkanes to oxygenates. More particularly, it is an object of the present invention to provide an alkane to oxygenate conversion process which has relatively low initial capital equipment costs and which has relatively low operating costs. These objects and others are accomplished in accordance with the invention described hereafter.

SUMMARY OF THE INVENTION

The present invention is a process for converting an alkane to an oxygenated product. The process comprises passing an alkane in a gas state over a first fixed bed containing a first bromide salt, which is in a solid state and is preferably fixed on a support, to produce an alkyl bromide, a hydrobromic acid, and a second bromide salt. The first and second bromide salts include a transition metal which has a higher valence state and a lower valence state. The transition metal is at the higher valence state in the first bromide salt and at the lower valence state in the second bromide salt. The second bromide salt produced above is retained in the first fixed bed in a solid state, while the alkyl bromide and hydrobromic acid are conveyed from the first fixed bed in a gas state to a second fixed bed.

The hydrobromic acid is passed over the second fixed bed containing a metal oxide, which is in a solid state and is preferably fixed on a support, to produce water in a gas state (i.e., steam) and the first bromide salt. The metal oxide contained in the second fixed bed includes a metal which is preferably a transition metal or an alkaline earth metal. For example, the metal of the metal oxide may be essentially identical to the transition metal of the first and second bromide salts.

The alkyl bromide is likewise passed over the second fixed bed in the presence of the steam to produce the first bromide salt and an oxygenated product, which is preferably an alcohol or an ether. The first bromide salt produced above is retained in the second fixed bed in a solid state, while the oxygenated product is conveyed from the second fixed bed in a gas state. The oxygenated product may be condensed downstream of the second fixed bed and recovered as a desirable liquid product.

The metal oxide in the second fixed bed is regenerated by passing oxygen, preferably in air, over the second fixed bed. The oxygen reacts with the first bromide salt in the second fixed bed to produce the metal oxide in a solid state and bromine in a gas state. The metal oxide is retained in the second fixed bed, while the bromine is conveyed from the second fixed bed to the first fixed bed. The first bromide salt in the first fixed bed is regenerated by passing the bromine over the first fixed bed. The bromine reacts with the second bromide salt in the first fixed bed to produce the first bromide salt, which is retained in the first fixed bed in a solid state.

In a preferred embodiment, the first and second fixed beds are purged before regenerating the first bromide salt in the first fixed bed and the metal oxide in the second fixed bed by passing an unreactive gas over the first and second fixed beds to remove any hydrocarbons therefrom. The first and second fixed beds are also preferably purged after regenerating the first bromide salt in the first fixed bed and the metal oxide in the second fixed bed by passing an unreactive gas over the first and second fixed beds to remove any oxygen therefrom.

In accordance with one embodiment, the first fixed bed and the second fixed bed are contained within a single reactor vessel. In accordance with an alternate embodiment, the first fixed bed is contained within a first reactor vessel and the second fixed bed is contained within a second reactor vessel.

The process may further comprise cyclically repeating one or more times the steps of passing the alkane over the first fixed bed, passing the alkyl bromide and the hydrobromic acid over the second fixed bed, and regenerating the first bromide salt in the first fixed bed and the metal oxide in the second fixed bed. The steps of passing the alkane over the first fixed bed and passing the alkyl bromide and the hydrobromic acid over the second fixed bed are preferably suspended while regenerating the first bromide salt in the first fixed bed and the metal oxide in the second fixed bed. Conversely, the steps of regenerating the first bromide salt in the first fixed bed and the metal oxide in the second fixed bed are preferably suspended while passing the alkane over the first fixed bed and passing the alkyl bromide and the hydrobromic acid over the second fixed bed.

In accordance with an alternate embodiment, the alkane is passed over a third fixed bed containing a third bromide salt and an alkyl bromide and hydrobromic acid resulting from the third fixed bed are passed over a fourth fixed bed containing a second metal oxide, while the steps of passing the alkane over the first fixed bed and passing the alkyl bromide and the hydrobromic acid over the second fixed bed are suspended. The first and third bromide salts may be essentially identical or the third bromide salt may include a transition metal different from the transition metal of the first bromide salt. The metal oxide contained in the second fixed bed is a first metal oxide and the first and second metal oxides may be essentially identical or the second metal oxide may include a metal different from the metal of the first metal oxide. The process of this embodiment further comprises regenerating the third bromide salt in the third fixed bed and the second metal oxide in the fourth fixed bed while passing the alkane over the first fixed bed and passing the alkyl bromide and the hydrobromic acid over the second fixed bed.

In accordance with yet another alternate embodiment, the process for converting an alkane to an oxygenated product comprises reacting an alkane with a first bromide salt in a first reactor to produce an alkyl bromide, a hydrobromic acid, and a second bromide salt. The first and second bromide salts include a transition metal having a higher valence state and a lower valence state. The transition metal is at the higher valence state in the first bromide salt and at the lower valence state in the second bromide salt. The hydrobromic acid is reacted with a metal oxide in a second reactor to produce water and the first bromide salt. The alkyl bromide is reacted with the metal oxide and the water in the second reactor to produce an oxygenated product and the first bromide salt. The first and second reactors are purged with an unreactive gas to remove any hydrocarbons from the first and second reactors. The metal oxide is regenerated by reacting oxygen with the first bromide salt in the second reactor to produce the metal oxide and bromine. The first bromide salt is regenerated by reacting the bromine with the second bromide salt in the first reactor to produce the first bromide salt. The first and second reactors are purged again with an unreactive gas to remove any oxygen from the first and second reactors.

In accordance with one embodiment, the first reactor and the second reactor are integrally included within a single reactor vessel. In accordance with an alternate embodiment, the first reactor is included within a first reactor vessel and the second reactor is included within a second reactor vessel separate from the first reactor vessel.

The present invention will be further understood from the drawings and the following detailed description.

DESCRIPTION OF PREFERRED EMBODIMENTS

Figure 1:
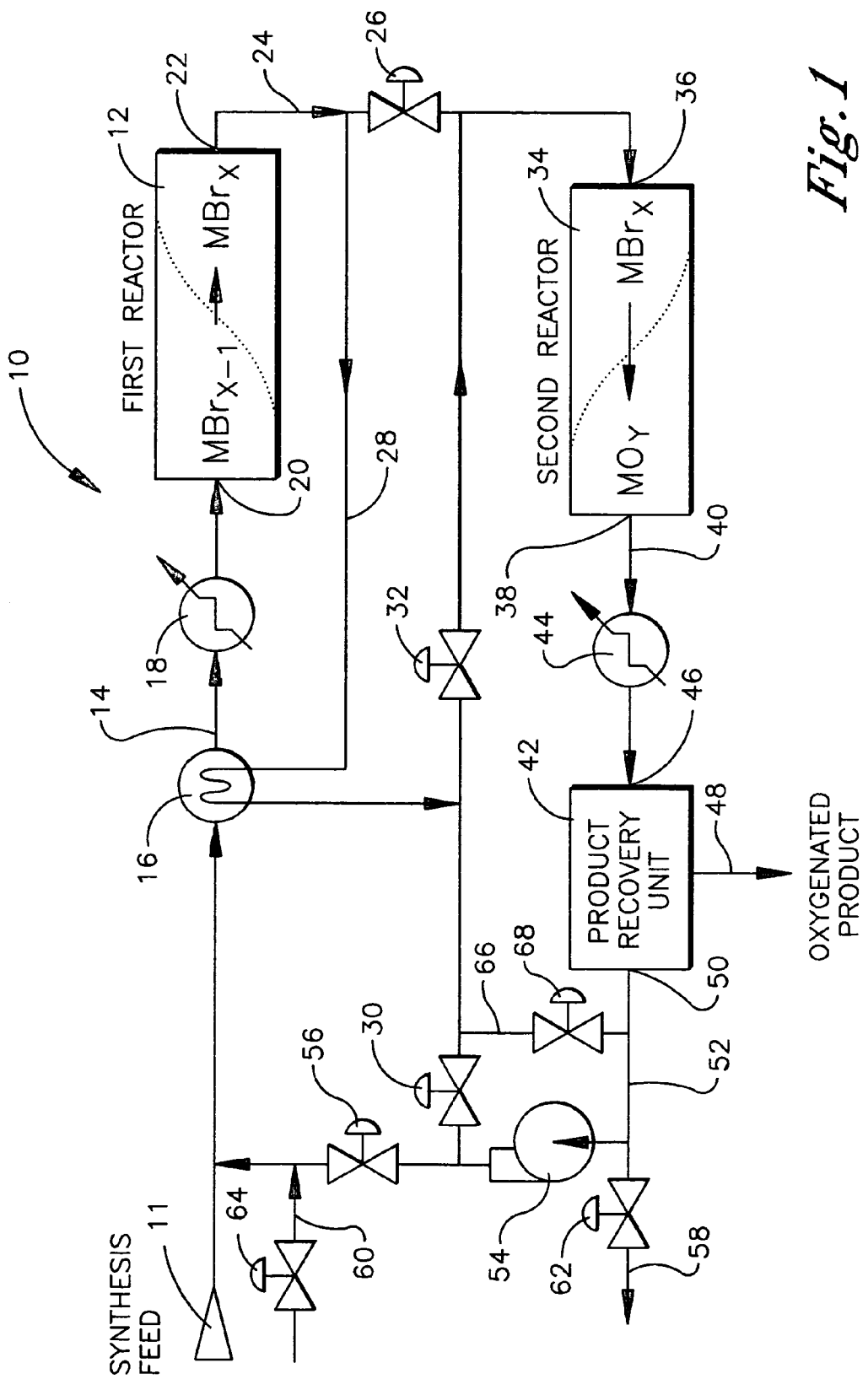
FIG. 1 is a schematic flow chart of a synthesis system for performing a synthesis step in a preferred embodiment of the process of the present invention.

The present invention is a process for converting alkanes in a gas state to oxygenated products in a liquid state. A preferred embodiment of the process generally comprises two steps, a synthesis step and a regeneration step. The synthesis step, alternately termed a reduction step, is shown and described hereafter with reference to FIG. 1, wherein a synthesis system for performing the synthesis step is shown and generally designated 10.

The synthesis step is initiated by delivering a synthesis feed to a synthesis feed port 11 of the synthesis system 10. The synthesis feed is in a gas state and comprises one or more alkanes, such as methane, ethane, propane, and the like. A preferred synthesis feed is natural gas consisting predominantly of methane and essentially free of pentane, heavier alkanes and sulfur-containing compounds.

The synthesis feed is conveyed from the synthesis feed port 11 to a first reactor 12 via a first reactor synthesis inlet line 14. An in-line counter-current synthesis heat exchanger 16 and an in-line synthesis trim heater 18 are serially positioned in the first reactor synthesis inlet line 14 upstream of the first reactor 12, to preheat the synthesis feed. The synthesis heat exchanger 16 and synthesis heater 18 preferably preheat the synthesis feed from a temperature range of about 0 to 100° C. to a temperature range of about 250 to 600° C. The preheated synthesis feed continues via the first reactor synthesis inlet line 14 to a first reactor synthesis inlet port 20 through which the preheated synthesis feed is fed to the first reactor 12.

The first reactor 12 is a vessel enclosing a first fixed bed. The first fixed bed comprises a stationary first support and a first bromide salt fixed on the stationary first support. The metal of the first bromide salt is a transition metal having at least two valence states, i.e., a higher valence state and a lower valence state. The metal is capable of forming the first bromide salt when the metal is at the higher valence state and is further capable of forming the second bromide salt when the metal is at the lower valence state. Preferred transition metals satisfying these criteria and having utility herein include Cu, Fe, W, V, Ni, Co, and Mn. More preferred from among these transition metals are Cu or Fe. The stationary first support for the first bromide salt may be formed from any suitable support material within the purview of the skilled artisan. A preferred first support is formed from alumina.

The preheated synthesis feed, which is in a gas state, passes over the stationary first fixed bed within the first reactor 12, which includes the first bromide salt in a solid state. The term "passes over" as used herein means that the gas not only flows over the top of the fixed bed and contacts the solids thereon, but that the gas also flows through the interstitial passageways within the interior of the fixed bed and contacts the solids therein. The first fixed bed is at an elevated temperature preferably within a range of about 250 to 600° C. and at a pressure within a range of about 1 to 20 atm. The synthesis feed reacts endothermically with the first bromide salt under these conditions to produce an alkyl bromide, a hydrobromic acid, and the second bromide salt. The metal of the second bromide salt is the same metal of the first bromide salt, but at the lower valence state of the metal. The alkyl bromide is in a gas state, the hydrobromic acid is in a gas state (i.e., vapor state), and the second bromide salt is in a solid state.

Equation 1 below is an exemplary reaction between the synthesis feed and the first bromide salt, wherein the synthesis feed is methane and the first bromide salt is copper (II) bromide.

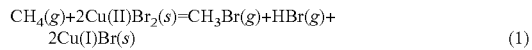

$$CH_4(g) + 2Cu(II)Br_2(s) = CH_3Br(g) + HBr(g) + 2Cu(I)Br(s) \quad (1)$$

ΔH=+16.1 kcal $K_{eq}$=11,000 at 300° C.

The resulting fluids, i.e., the alkyl bromide and the hydrobromic acid as well as any excess synthesis feed, which are termed in total the first reactor synthesis outlet fluids, are withdrawn from the first reactor 12 via a first reactor synthesis outlet port 22, while the resulting solids, i.e., the second bromide salt, are retained on the first support of the first fixed bed in the first reactor 12. The first reactor synthesis outlet fluids are conveyed downstream via a first reactor synthesis outlet line 24 to an in-line valve 26. In a preferred embodiment, the in-line valve 26 is closed, thereby diverting the first reactor synthesis outlet fluids to the synthesis heat exchanger 16 via a heat exchanger loop 28. The first reactor synthesis outlet fluids are cooled within the synthesis heat exchanger 16 to a temperature range of about 100 to 300° C., while simultaneously preheating the synthesis feed from the synthesis feed port 11 as described above.

The cooled first reactor synthesis outlet fluids are conveyed from the synthesis heat exchanger 16 back to the first reactor synthesis outlet line 24 downstream of the closed in-line valve 26 via the heat exchanger loop 28, which is additionally provided with in-line valves 30, 32. To direct the cooled first reactor synthesis outlet fluids back to the first reactor synthesis outlet line 24, the in-line valve 30 is closed, while the in-line valve 32 is open. The first reactor synthesis outlet line 24 conveys the cooled first reactor synthesis outlet fluids to a second reactor 34 and the cooled first reactor synthesis outlet fluids are fed into the second reactor 34 via a second reactor synthesis inlet port 36.

In accordance with an alternate embodiment, the first reactor synthesis outlet fluids can by-pass the heat exchanger loop 28 and proceed directly from the first reactor synthesis outlet port 22 to the second reactor synthesis inlet port 36 via the first reactor synthesis outlet line 24 without being cooled in the synthesis heat exchanger 16. This embodiment is effected by opening the in-line valve 26 and closing the in-line valve 32, while maintaining the in-line valve 30 closed.

The second reactor 34 is a vessel enclosing a second fixed bed. The second fixed bed comprises a stationary second support and a metal oxide fixed on the stationary second support. The metal of the metal oxide is a transition metal or an alkaline earth metal which is capable of forming an oxidizable bromide salt. Preferred transition metals satisfying these criteria and having utility herein include Cu, Zn, Co, V, Ni, and Mn. More preferred from among these transition metals are Cu or Zn. Preferred alkaline earth metals satisfying these criteria and having utility herein include Ca and Mg. It is apparent from the above that the metal oxide selected for the second fixed bed in the second reactor 34 may have the same metal as the first bromide salt selected for the first fixed bed in the first reactor 12, if desired. The stationary second support for the metal oxide may be formed from any suitable support material within the purview of the skilled artisan. A preferred support is formed from a zeolite.

The hydrobromic acid, which is in a gas state, passes over the stationary second fixed bed within the second reactor 34, which includes the metal oxide in a solid state. The second fixed bed is at an elevated temperature preferably within a range of about 100 to 300° C. and at a pressure within a range of about 1 to 20 atm. The hydrobromic acid reacts exothermically with the metal oxide of the second fixed bed at these conditions to produce water and the first bromide salt. The water is in a gas state (i.e., in a vapor state as steam) and the first bromide salt is in a solid state.

The alkyl bromide, which is in a gas state, passes over the stationary second fixed bed within the second reactor 34 simultaneously with the hydrobromic acid. The alkyl bromide reacts exothermically at the above recited conditions of the second fixed bed with the metal oxide of the second fixed bed and the water from the hydrobromic acid reaction to produce the desired alcohol and ether products, which are termed in total the oxygenated products, and the first bromide salt. The oxygenated products are in a gas state and the first bromide salt is in a solid state. The excess alkane, if any, passes through the second reactor 34 without undergoing any significant further reaction. The precise species of the alcohols and ethers in the oxygenated products correspond to the species of the alkanes in the synthesis feed. For example, methyl alcohol and/or dimethyl ether in the oxygenated products is derived from methane in the synthesis feed, ethyl alcohol and/or diethyl ether in the oxygenated products is derived from ethane in the synthesis feed, and so on.

It is noted that water, preferably in the form of steam, may optionally be added to the first reactor synthesis outlet fluids at a point upstream of the second reactor 34 to influence the product selectivity of the reaction between the alkyl bromide, metal oxide, and water. Increasing the amount of added steam decreases the selectivity to dimethyl ether and increases the selectivity to alcohol. For example, the addition of 0 to 5 moles of steam per mole of methyl bromide results in a higher selectivity to dimethyl ether, i.e., in a range of about 70 to 80%, and a lower selectivity to alcohol, i.e., in a range of about 20 to 30%. The addition of 5 to 15 moles of steam per mole of methyl bromide results in an increased selectivity to alcohol, i.e., in a range of about 30 to 50%, and a decreased selectivity to dimethyl ether, i.e., in a range of about 70 to 50%.

Equation 2 below is an exemplary reaction between the hydrobromic acid and the metal oxide, wherein the hydrobromic acid is the product of equation 1 and the metal oxide is copper oxide. Equation 3 is an exemplary reaction between the alkyl bromide, metal oxide, and water, wherein the alkyl bromide is the product of equation 1 and the metal oxide is copper oxide.

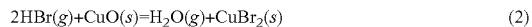
(2)

$\Delta H = -36.6$ kcal
$K_{eq} = 2.2 \times 10^{12}$ at 150° C.

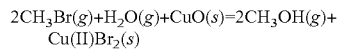
(3)

$\Delta H = -16.1$ kcal
$K_{eq} = 232$ at 150° C.

The resulting fluids, i.e., the oxygenated products and any excess alkane as well as any unreacted alkyl bromide, which are termed in total the second reactor synthesis outlet fluids, are withdrawn from the second reactor 34 via a second reactor synthesis outlet port 38, while the resulting solids, i.e., the first bromide salt, are retained on the second support of the second fixed bed in the second reactor 34. The second reactor synthesis outlet fluids are conveyed downstream via a second reactor synthesis outlet line 40 to a product recovery unit 42. An in-line trim cooler 44 is provided in the second reactor synthesis outlet line 40 to cool the second reactor synthesis outlet fluids upstream of the product recovery unit 42, thereby removing at least a portion of the heat of reaction and condensing the oxygenated products in the second reactor synthesis outlet fluids. The cooler 44 preferably cools the second reactor synthesis outlet fluids from a temperature range of about 100 to 300° C. to a temperature range of about 0 to 50° C. The cooled second reactor synthesis outlet fluids containing the condensed oxygenated products continue out the cooler 44 via the second reactor synthesis outlet line 40 to a product recovery unit inlet port 46 through which the cooled second reactor synthesis outlet fluids are fed to the product recovery unit 42.

The product recovery unit 42 is an appropriate type of conventional separator selected in accordance with criteria within the purview of a skilled artisan for the present application. The condensed oxygenated products are separated from the remainder of the second reactor synthesis outlet fluids in the product recovery unit 42 and discharged from the product recovery unit 42 in a liquid state via an oxygenated product outlet port 48. The liquid oxygenated products are recovered at the oxygenated product outlet port 48 for subsequent beneficial use.

A synthesis effluent gas is also discharged from the product recovery unit 42 via a synthesis effluent outlet port 50. The synthesis effluent gas is comprised primarily of any excess alkane and unreacted alkyl bromide and is preferably substantially free of any inert gases or free oxygen. The synthesis effluent gas is conveyed via a synthesis recycle line 52 to an in-line synthesis recycle blower 54. An in-line valve 56 in the synthesis recycle line 52 downstream of the synthesis recycle blower 54, in cooperation with the in-line valve 30, enables selective recycling of the synthesis effluent gas to the first reactor 12 and/or the second reactor 34 for selectivity control and improved overall conversion of the reactions therein.

In a preferred embodiment, a portion of the synthesis effluent gas is mixed with the synthesis feed at the synthesis feed port 11 and recycled to the first reactor 12 via the first reactor synthesis inlet line 14. The remaining portion of the synthesis effluent gas is mixed with the cooled first reactor synthesis outlet fluids in the heat exchanger loop 28 and recycled to the second reactor 34 via the first reactor synthesis outlet line 24.

The synthesis recycle line 52 is further provided with a synthesis vent port 58 downstream of the in-line valve 26 and a purge gas inlet port 60 downstream of the synthesis recycle blower 54. Fluid communication between the synthesis vent port 58 and the synthesis recycle line 52 is selectively controlled by an in-line valve 62. Fluid communication between the purge gas inlet port 60 and the synthesis recycle line 52 is similarly selectively controlled by an in-line valve 64. Gases within the synthesis system 10 can be selectively discharged as desired from the synthesis recycle line 52 into the surrounding environment or an associated bromine-containing compound recovery system (not shown) via the synthesis vent port 58 when the in-line valve 62 is open. After recovering any bromine-containing compounds are recovered, the resulting gas may be used for fuel or incinerated. A purge gas, such as nitrogen or any other gas which is inert (i.e., unreactive) with the reactants in the synthesis system 10, can be selectively introduced into the synthesis recycle line 52 via the purge gas inlet port 60 when the in-line valve 64 is open. An optional by-pass line 66 links the synthesis recycle line 52 and the heat exchanger loop 28. Fluid communication between the synthesis recycle line 52 and the heat exchanger loop 28 is selectively controlled by an in-line valve 68.

The synthesis step is completed when an insufficient amount of the first bromide salt remains in the first fixed bed of the first reactor 12 to provide adequate conversion of the synthesis feed and/or an insufficient amount of metal oxide remains in the second fixed bed of the second reactor 34 to provide adequate conversion of the hydrobromic acid. At this point the synthesis step is terminated and a reactor purge described hereafter is performed.

The reactor purge comprises introducing the purge gas into the synthesis system 10 via the purge gas inlet port 60 upon termination of the synthesis step, but before initiation of the regeneration step. The purge gas circulates through the synthesis system 10 to effectively purge the first and second reactors 12, 34 of reactive gases, and in particular hydrocarbon gases. Thus, the reactor purge prevents undesirable mixing of hydrocarbon gases with oxygen in the first or second reactors 12, 34 when air or pure oxygen is introduced into the first or second reactors 12, 34 during the regeneration step described hereafter. Circulating the purge gas through the first and second reactors 12, 34 during the reactor purge also effectively precools the first fixed bed in the first reactor 12 and preheats the second fixed bed in the second reactor 34 to their desired temperatures for the regeneration step.

Figure 2:
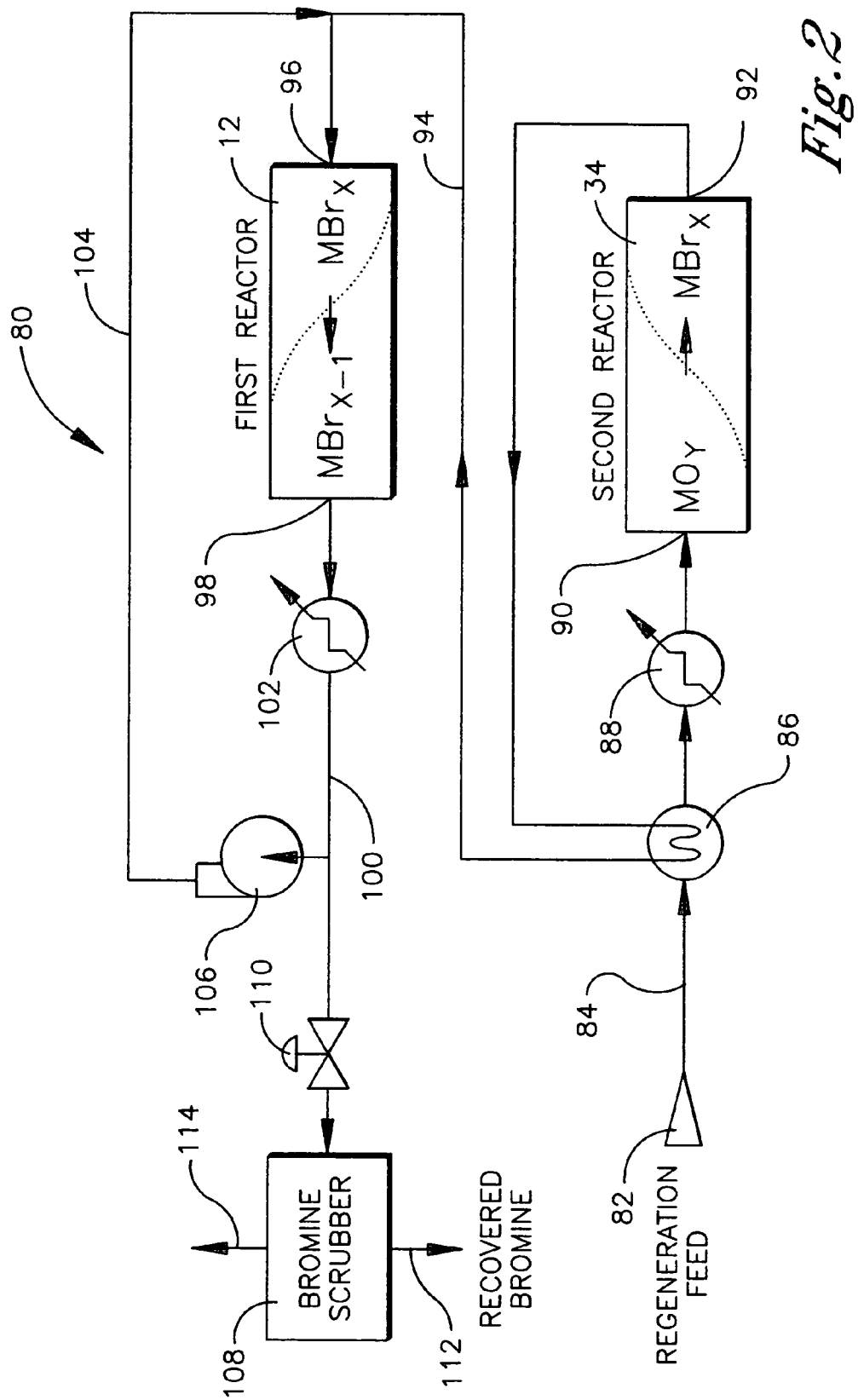
FIG. 2 is a schematic flow chart of a regeneration system for performing a regeneration step in a preferred embodiment of the process of the present invention.

The regeneration step, alternately termed an oxidation step, is shown and described hereafter with reference to FIG. 2, wherein a regeneration system for performing the regeneration step is shown and generally designated 80. The first and second reactors 12 and 34, respectively, shown and described in the synthesis system 10 of FIG. 1 are utilized in the regeneration system 80 as well. Accordingly, the first and second reactors are designated by the same reference numbers 12 and 34, respectively, in FIG. 2 as in FIG. 1.

The regeneration step is initiated by delivering a regeneration feed to a regeneration feed port 82 of the regeneration system 80. The regeneration feed is a dilute source of free oxygen, such as air or pure oxygen. A preferred regeneration feed is air which is conveyed from the regeneration feed port 82 to the second reactor 34 via a second reactor regeneration inlet line 84. An in-line counter-current regeneration heat exchanger 86 and an in-line regeneration trim heater 88 are serially positioned in the second reactor regeneration inlet line 84 upstream of the second reactor 34, to preheat the regeneration feed. The regeneration heat exchanger 86 and regeneration heater 88 preferably preheat the regeneration feed from a temperature range of about 0 to 50° C. to a temperature range of about 200 to 500° C. The preheated regeneration feed continues through the second reactor regeneration inlet line 84 to a second reactor regeneration inlet port 90 through which the preheated regeneration feed is fed to the second reactor 34.

The free oxygen of the preheated regeneration feed, which is in a gas state, passes over the stationary second fixed bed within the second reactor 34, which includes the first bromide salt retained in a solid state on the second support of the second fixed bed. The second fixed bed is at a temperature preferably within a range of about 150 to 450° C. and at a pressure within a range of about 1 to 20 atm. The free oxygen reacts endothermically with the first bromide salt of the second fixed bed at these conditions to produce the metal oxide and bromine. The heat source for the endothermic reaction is at least in part the sensible heat remaining in the second fixed bed of the second reactor 34 after the synthesis step and the reactor purge. The bromine is in a gas state and the metal oxide is in a solid state.

Equation 4 below is an exemplary reaction between the free oxygen of the regeneration feed and the first bromide salt, wherein the first bromide salt is the product of equation 3.

$$2Cu(II)Br_2(s) + O_2(g) = 2CuO(s) + 2Br_2(g) \tag{4}$$

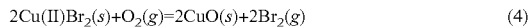

$\Delta H = +5.1$ kcal
$K_{eq} = 1,900$ at 300° C.
$\Delta H = +5.9$ kcal
$K_{eq} = 350$ at 150° C.

The resulting fluids, i.e., the bromine and any residual purge gas, which are termed in total the second reactor regeneration outlet fluids, are withdrawn from the second reactor 34 via a second reactor regeneration outlet port 92, while the resulting solids, i.e., the metal oxide, are retained on the second support of the second fixed bed in the second reactor 34, thereby regenerating the second fixed bed. The second reactor regeneration outlet fluids are conveyed downstream via a second reactor regeneration outlet line 94 to the regeneration heat exchanger 86. The second reactor regeneration outlet fluids are cooled within the regeneration heat exchanger 86 to a temperature range of about 100 to 250° C., while simultaneously preheating the regeneration feed from the regeneration feed port 82 as described above.

The cooled second reactor regeneration outlet fluids are conveyed from the regeneration heat exchanger 86 via the second reactor regeneration outlet line 94 to the first reactor 12 and the cooled second reactor regeneration outlet fluids are fed into the first reactor 12 via a first reactor regeneration inlet port 96. The bromine, which is in a gas state, passes over the stationary first fixed bed within the first reactor 12, which includes the second bromide salt retained in a solid state on the first support of the first fixed bed. The first fixed bed is at a temperature preferably within a range of about 100 to 250° C. and at a pressure within a range of about 1 to 2 atm. The bromine reacts exothermically with the second bromide salt of the second fixed bed at these conditions to produce the first bromide salt in a solid state.

Equation 5 below is an exemplary reaction between the bromine and the second bromide salt, wherein the second bromide salt is the product of equation 1.

$$2Cu(I)Br(s) + Br_2(g) = 2Cu(II)Br_2(s) \tag{5}$$

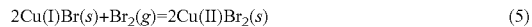

$\Delta H = -23.4$ kcal
$K_{eq} = 327$ at 150° C.
$\Delta H = -23.3$ kcal
$K_{eq} = 13,500$ at 100° C.

The resulting fluids, i.e., the residual purge gas as well any unreacted bromine, which are termed in total the first reactor regeneration outlet fluids, are withdrawn from the first reactor 12 via a first reactor regeneration outlet port 98, while the resulting solids, i.e., the first bromide salt, are retained on the first support of the first fixed bed in the first reactor 12, thereby regenerating the first fixed bed. The first reactor regeneration outlet fluids are conveyed downstream via a first reactor regeneration outlet line 100 to an in-line regeneration trim cooler 102. The first reactor regeneration outlet fluids are cooled within the regeneration trim cooler 102 to a temperature range of about 100 to 250° C., to at least partially remove the heat of reaction due to the regeneration reaction in the first reactor 12.

In a preferred embodiment, a portion of the first reactor regeneration outlet fluids are conveyed via a regeneration recycle line 104 to an in-line regeneration recycle blower 106. The regeneration recycle blower 106 conveys the portion of the first reactor regeneration outlet fluids to the second reactor regeneration outlet line 94 via the regeneration recycle line 104, where the portion of the first reactor regeneration outlet fluids mix with the second reactor regeneration outlet fluids before being recycled to the first reactor 12 via the first reactor regeneration inlet port 96. The remaining non-recycled portion of the first reactor regeneration outlet fluids are conveyed to a bromine scrubber 108 via the first reactor regeneration outlet line 100 having an in-line valve 110. The bromine scrubber 108 separates the unreacted bromine from the first reactor regeneration outlet fluids. The separated bromine dissolved in an aqueous solution is recovered from the bromine scrubber 108 via a bromine outlet port 112 for subsequent beneficial use. The remaining first reactor regeneration outlet fluids, termed the regeneration effluent gas, which is comprised primarily of residual purge gas, is discharged from the regeneration system via a regeneration vent port 114.

The regeneration step is completed when a sufficient amount of the first bromide salt is regenerated in the first fixed bed of the first reactor 12 to provide adequate conversion of the synthesis feed and a sufficient amount of the metal oxide is regenerated in the second fixed bed of the second reactor 34 to provide adequate conversion of the hydrobromic acid and alkyl bromide. At this point the regeneration step is terminated and the reactor purge is preferably performed. In particular, the purge gas is reintroduced into the first and second reactors 12, 34 via the purge gas inlet port 60 of the synthesis system 10 in substantially the same manner as recited above. The synthesis and regeneration steps are preferably performed repeatedly in a continuous cyclic manner.

The synthesis and regeneration systems 10, 80 are shown and described above as a separate set of paired synthesis and regeneration systems for purposes of illustration. However, the process of the present invention is not limited to any one configuration of synthesis and regeneration systems. Thus, for example, it is apparent to the skilled artisan that the synthesis and regeneration systems can be integrated into a single synthesis/regeneration system within the scope of the present invention. An integrated synthesis/regeneration system economizes by utilizing a number of system components (in addition to the first and second reactors 12, 34) in both the synthesis and regeneration steps. For example, it is within the scope of the present invention to provide only a single port at each end of the first reactor. One port is employed as the first reactor synthesis outlet port in the synthesis step and as the first reactor regeneration inlet port in the regeneration step. The opposite port is employed as the first reactor synthesis inlet port in the synthesis step and the first reactor regeneration outlet port in the regeneration step.

It is similarly within the scope of the present invention to provide only a single port at each end of the second reactor. One port is employed as the second reactor synthesis outlet port of the synthesis step and as the second reactor regeneration inlet port of the regeneration step. The opposite port is employed as the second reactor synthesis inlet port of the synthesis step and as the second reactor regeneration outlet port of the regeneration step. Such configurations require the addition of appropriate cooperative lines and valving, which are readily within the purview of the skilled artisan.

As another example, it is within the scope of the present invention to employ an integrated synthesis/regeneration system having only a single trim heater, trim cooler, heat exchanger, and recycle blower. Each component performs the dual functions of the synthesis step and the regeneration step. In particular, each component functions dually as both trim heaters 18, 88, both trim coolers 44, 102, both heat exchangers 16, 86 and both recycle blowers 54, 106, respectively, when appropriate cooperative lines and valving are additionally provided.

In accordance with the embodiment of the present invention shown and described above, the process is practiced by providing an intermittent synthesis feed to a single set of paired synthesis and regeneration systems or to a single integrated synthesis/regeneration system. The synthesis feed is interrupted whenever the single set of paired systems or integrated system transitions from the synthesis step to the regeneration step and resumes whenever the single set of paired systems or integrated system transitions from the regeneration step back to the synthesis step.

In accordance with an alternate preferred embodiment, two parallel sets of paired synthesis and regeneration systems or two parallel integrated synthesis/regeneration systems are provided. Duplication of the systems permits continuous processing of an uninterrupted synthesis feed in a staggered sequence. Whenever one set of paired systems or one integrated system transitions from the synthesis step to the regeneration step, the synthesis feed shifts to the other set of paired systems or the other integrated system, which has transitioned from the regeneration step to the synthesis step. When the other set of paired systems or the other integrated system transitions from the synthesis step back to the regeneration step, the synthesis feed shifts back to the original set of paired systems or the original integrated system, which has transitioned from the regeneration step back to the synthesis step.

In accordance with the embodiment of the present invention shown and described above, the first reactor and the second reactor are two separate and distinct reaction vessels, which contain the first fixed bed and the second fixed bed, respectively. In accordance with an alternate embodiment, the first and second reactors are serially integrated in a single reactor vessel, which contains the first fixed bed and the second fixed bed as serially contiguous fixed beds within the single reactor vessel.

While the forgoing preferred embodiments of the invention have been described and shown, it is understood that alternatives and modifications, such as those suggested and others, may be made thereto and fall within the scope of the invention.

I claim:

1. A process for converting an alkane to an oxygenated product comprising:
    passing an alkane in a gas state over a first fixed bed containing a first bromide salt in a solid state to produce an alkyl bromide in a gas state, a hydrobromic acid in a gas state and a second bromide salt in a solid state, wherein said second bromide salt is retained in said first fixed bed and further wherein said first and second bromide salts include a transition metal having a higher valence state and a lower valence state and said transition metal is at said higher valence state in said first bromide salt and at said lower valence state in said second bromide salt;
    passing said hydrobromic acid over a second fixed bed containing a metal oxide in a solid state to produce water in a gas state and said first bromide salt in a solid state, wherein said first bromide salt is retained in said second fixed bed;
    passing said alkyl bromide over said second fixed bed in the presence of said water to produce an oxygenated product in a gas state and said first bromide salt in a solid state, wherein said first bromide salt is retained in said second fixed bed;
    regenerating said metal oxide in said second fixed bed by passing oxygen over said second fixed bed, thereby reacting said oxygen with said first bromide salt in said second fixed bed to produce said metal oxide in a solid state and bromine in a gas state, wherein said metal oxide is retained in said second fixed bed; and
    regenerating said first bromide salt in said first fixed bed by passing said bromine over said first fixed bed, thereby reacting said bromine with said second bromide salt in said first fixed bed to produce said first bromide salt, wherein said first bromide salt is retained in said first fixed bed.

2. The process of claim 1 wherein said first bromide salt in said first fixed bed is fixed on a support.

3. The process of claim 1 wherein said first fixed bed is purged by passing an unreactive gas over said first fixed bed to remove any hydrocarbons from said first fixed bed before regenerating said first bromide salt in said first fixed bed and said metal oxide in said second fixed bed.

4. The process of claim 1 wherein said first fixed bed is purged by passing an unreactive gas over said first fixed bed to remove any oxygen from said first fixed bed after regenerating said first bromide salt in said first fixed bed and said metal oxide in said second fixed bed.

5. The process of claim 1 wherein said metal oxide in said second fixed bed is fixed on a support.

6. The process of claim 1 wherein said second fixed bed is purged by passing an unreactive gas over said second fixed bed to remove any hydrocarbons from said second fixed bed before regenerating said first bromide salt in said first fixed bed and said metal oxide in said second fixed bed.

7. The process of claim 1 wherein said second fixed bed is purged by passing an unreactive gas over said second fixed bed to remove any oxygen from said second fixed bed after regenerating said first bromide salt in said first fixed bed and said metal oxide in said second fixed bed.

8. The process of claim 1 wherein said oxygen is passed over said second fixed bed by passing air containing said oxygen over said second fixed bed.

9. The process of claim 1 wherein said oxygenated product is an alcohol or an ether.

10. The process of claim 1 wherein said metal oxide includes a metal and said metal of said metal oxide is a transition metal or an alkaline earth metal.

11. The process of claim 1 wherein said metal oxide includes a transition metal essentially identical to said transition metal of said first and second bromine salts.

12. The process of claim 1 wherein said first fixed bed and said second fixed bed are contained within a single reactor vessel.

13. The process of claim 1 wherein said first fixed bed is contained within a first reactor vessel and said second fixed bed is contained within a second reactor vessel.

14. The process of claim 1 further comprising cyclically repeating one or more times said steps of passing said alkane over said first fixed bed, passing said alkyl bromide and said hydrobromic acid over said second fixed bed, and regenerating said first bromide salt in said first fixed bed and said metal oxide in said second fixed bed.

15. The process of claim 1 wherein said steps of passing said alkane over said first fixed bed and passing said alkyl bromide and said hydrobromic acid over said second fixed bed are suspended while regenerating said first bromide salt in said first fixed bed and said metal oxide in said second fixed bed, and further wherein said steps of regenerating said first bromide salt in said first fixed bed and said metal oxide in said second fixed bed are suspended while passing said alkane over said first fixed bed and passing said alkyl bromide and said hydrobromic acid over said second fixed bed.

16. The process of claim 15 further comprising passing said alkane over a third fixed bed containing a third bromide salt and passing an alkyl bromide and a hydrobromic acid from said third fixed bed over a fourth fixed bed containing a second metal oxide while said steps of passing said alkane over said first fixed bed and passing said alkyl bromide and said hydrobromic acid over said second fixed bed are suspended, wherein said first and third bromide salts are essentially identical or said third bromide salt includes a transition metal different from said transition metal of said first bromide salt and said metal oxide contained in said second fixed bed is a first metal oxide and said first and second metal oxides are essentially identical or said second metal oxide includes a metal different from said metal of said first metal oxide.

17. The process of claim 16 further comprising regenerating said third bromide salt in said third fixed bed and said second metal oxide in said fourth fixed bed while passing said alkane over said first fixed bed and passing said alkyl bromide and said hydrobromic acid over said second fixed bed.

18. A process for converting an alkane to an oxygenated product comprising:
reacting an alkane with a first bromide salt in a first reactor to produce an alkyl bromide, a hydrobromic acid, and a second bromide salt, wherein said first and second bromide salts include a transition metal having a higher valence state and a lower valence state and said transition metal is at said higher valence state in said first bromide salt and at said lower valence state in said second bromide salt;
reacting said hydrobromic acid with a metal oxide in a second reactor to produce water and said first bromide salt;
reacting said alkyl bromide with said metal oxide and said water in said second reactor to produce an oxygenated product and said first bromide salt;
purging said first and second reactors with an unreactive gas to remove any hydrocarbons from said first and second reactors;
regenerating said metal oxide in said second reactor by reacting oxygen with said first bromide salt in said second reactor to produce said metal oxide and bromine;
regenerating said first bromide salt in said first reactor by reacting said bromine with said second bromide salt in said first reactor to produce said first bromide salt; and
purging said first and second reactors with an unreactive gas to remove any oxygen from said first and second reactors.

19. The process of claim 18 wherein said first bromide salt in said first reactor is fixed on a support in a first fixed bed.

20. The process of claim 18 wherein said metal oxide in said second reactor is fixed on a support in a second fixed bed.

21. The process of claim 18 wherein said oxygen reacting with said first bromide salt in said second reactor is contained within air fed to said second reactor.

22. The process of claim 18 wherein said oxygenated product is an alcohol or an ether.

23. The process of claim 18 wherein said metal oxide includes a metal and said metal of said metal oxide is a transition metal or an alkaline earth metal.

24. The process of claim 18 wherein said metal oxide includes a transition metal essentially identical to said transition metal of said first and second bromine salts.

25. The process of claim 18 wherein said first reactor and said second reactor are included within a single reactor vessel.

26. The process of claim 18 wherein said first reactor is included within a first reactor vessel and said second reactor is included within a second reactor vessel.

27. The process of claim 18 further comprising cyclically repeating one or more times said steps of reacting said alkane in said first reactor, reacting said alkyl bromide and said hydrobromic acid in said second reactor, purging said first and second reactors, regenerating said metal oxide in said second reactor and said first bromide salt in said first reactor, and purging said first and second reactors.

28. The process of claim 18 wherein said steps of reacting said alkane in said first reactor and reacting said alkyl bromide and said hydrobromic acid in said second reactor are suspended while regenerating said metal oxide in said second reactor and said first bromide salt in said first reactor, and further wherein said steps of regenerating said metal oxide in said second reactor and said first bromide salt in said first reactor are suspended while reacting said alkane in said first reactor and reacting said alkyl bromide and said hydrobromic acid in said second reactor.

29. The process of claim 28 further comprising reacting said alkane in a third reactor with a third bromide salt and reacting an alkyl bromide and a hydrobromic acid from said third reactor in a fourth reactor with a second metal oxide while said steps of reacting said alkane in said first reactor and reacting said alkyl bromide and said hydrobromic acid in said second reactor are suspended, wherein said first and third bromide salts are essentially identical or said third bromide salt includes a transition metal different from said transition metal of said first bromide salt and said metal oxide in said second reactor is a first metal oxide and said first and second metal oxides are essentially identical or said second metal oxide includes a metal different from said metal of said first metal oxide.

30. The process of claim 29 further comprising regenerating said second metal oxide in said fourth reactor and said third bromide salt in said third reactor while reacting said alkane in said first reactor and reacting said alkyl bromide and said hydrobromic acid in said second reactor.

31. A process for converting an alkane to an oxygenated product comprising:
passing an alkane in a gas state over a first fixed bed containing a first bromide salt in a solid state to produce an alkyl bromide in a gas state, a hydrobromic acid in a gas state and a second bromide salt in a solid state, wherein said second bromide salt is retained in said first fixed bed and further wherein said first and second bromide salts include a transition metal having a higher valence state and a lower valence state and said transition metal is at said higher valence state in said first bromide salt and at said lower valence state in said second bromide salt;
passing said hydrobromic acid over a second fixed bed containing a metal oxide in a solid state to produce water in a gas state and said first bromide salt in a solid state, wherein said first bromide salt is retained in said second fixed bed;
passing said alkyl bromide over said second fixed bed in the presence of said water to produce an oxygenated product in a gas state and said first bromide salt in a solid state, wherein said first bromide salt is retained in said second fixed bed;
purging said first and second fixed beds with an unreactive gas to remove any hydrocarbons from said first and second fixed beds;
regenerating said metal oxide in said second fixed bed by passing oxygen over said second fixed bed, thereby reacting said oxygen with said first bromide salt in said second fixed bed to produce said metal oxide in a solid state and bromine in a gas state, wherein said metal oxide is retained in said second fixed bed;
regenerating said first bromide salt in said first fixed bed by passing said bromine over said first fixed bed, thereby reacting said bromine with said second bromide salt in said first fixed bed to produce said first bromide salt, wherein said first bromide salt is retained in said first fixed bed; and
purging said first and second fixed beds with an unreactive gas to remove any hydrocarbons from said first and second fixed beds.

32. A process for converting an alkane to an oxygenated product comprising:
passing an alkane in a gas state over a first fixed bed containing a first bromide salt in a solid state to produce an alkyl bromide in a gas state, a hydrobromic acid in a gas state and a second bromide salt in a solid state, wherein said first and second bromide salts include a transition metal having a higher valence state and a lower valence state and said transition metal is at said higher valence state in said first bromide salt and at said lower valence state in said second bromide salt;
passing said hydrobromic acid over a second fixed bed containing a metal oxide in a solid state to produce water in a gas state and said first bromide salt in a solid state; and
passing said alkyl bromide over said second fixed bed in the presence of said water to produce an oxygenated product in a gas state and said first bromide salt in a solid state.

33. A process for regenerating materials used in an alkane to an oxygenated product conversion process comprising:
regenerating a metal oxide in a first fixed bed by passing oxygen over said first fixed bed, thereby reacting said oxygen with a first bromide salt in said first fixed bed to produce said metal oxide in a solid state and bromine in a gas state; and
regenerating said first bromide salt in a second fixed bed by passing said bromine over said second fixed bed, thereby reacting said bromine with a second bromide salt in said second fixed bed to produce said first bromide salt, wherein said first and second bromide salts include a transition metal having a higher valence state and a lower valence state and said transition metal is at said higher valence state in said first bromide salt and at said lower valence state in said second bromide salt.

* * * * *